(12) United States Patent
Desmazeau et al.

(10) Patent No.: US 7,232,799 B2
(45) Date of Patent: *Jun. 19, 2007

(54) STREPTOGRAMIN DERIVATIVES AND COMPOSITIONS THEREOF

(75) Inventors: Pascal Desmazeau, Tigery (FR); Baptiste Ronan, Clamart (FR); Eric Bacque, Morsang sur Orge (FR); Jean-Claude Barriere, Bures sur Yvette (FR)

(73) Assignee: Aventis Pharma SA, Antony (FR)

( * ) Notice: Subject to any disclaimer, the term of this patent is extended or adjusted under 35 U.S.C. 154(b) by 68 days.

This patent is subject to a terminal disclaimer.

(21) Appl. No.: 11/193,164

(22) Filed: Jul. 29, 2005

(65) Prior Publication Data

US 2005/0267181 A1    Dec. 1, 2005

Related U.S. Application Data

(60) Continuation of application No. 10/457,393, filed on Jun. 10, 2003, now Pat. No. 6,962,901, which is a division of application No. 10/024,186, filed on Dec. 21, 2001, now Pat. No. 6,596,717.

(60) Provisional application No. 60/262,645, filed on Jan. 22, 2001.

(30) Foreign Application Priority Data

Dec. 21, 2000    (FR) .................................. 00 16803

(51) Int. Cl.
*A61K 38/08*    (2006.01)

(52) U.S. Cl. .......................................................... 514/9

(58) Field of Classification Search ..................... 514/9
See application file for complete search history.

(56) References Cited

FOREIGN PATENT DOCUMENTS

| GB | 2206879 | 1/1989 |
|---|---|---|
| WO | WO01/02427 | 1/2001 |
| WO | WO01/10895 | 2/2001 |

*Primary Examiner*—Bruck Kifle
(74) *Attorney, Agent, or Firm*—Balaram Gupta

(57) ABSTRACT

The present invention discloses and claims pharmaceutical compositions comprising Group A streptogramin derivatives of formula (I) and salts thereof in combination with at least one natural group B streptogramin derivative

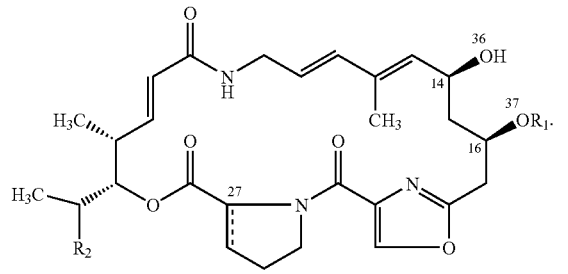

(I)

19 Claims, No Drawings

STREPTOGRAMIN DERIVATIVES AND COMPOSITIONS THEREOF

This application is a continuation of U.S. application Ser. No. 10/457,393, filed Jun. 10, 2003, now U.S. Pat. No. 6,962,901 now allowed, which is a division of U.S. application Ser. No. 10/024,186, filed Dec. 21, 2001, now U.S. Pat. No. 6,596,717 B2, issued, Jul. 22, 2003, which claims the benefit of U.S. Provisional Application No. 60/262,645, filed Jan. 22, 2001 and claims the benefit of priority of French Patent Application No. 00/16,803, filed Dec. 21, 2000, all of which are incorporated herein by reference in their entirety.

The present invention relates to group A streptogramin derivatives of formula (I):

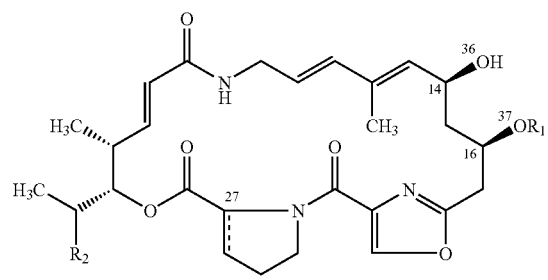

(I)

which have advantageous antibacterial activity.

Among the known streptogramins, pristinamycin (RP 7293), an antibacterial agent of natural origin produced by *Streptomyces pristinaespiralis,* was isolated for the first time in 1955. The pristinamycin sold under the name Pyostacine® comprises mainly pristinamycin IIA combined with pristinamycin IA.

Another antibacterial agent of the streptogramin class, virginiamycin, was isolated from *Streptomyces virginiae,* ATCC 13161 [Antibiotics and Chemotherapy, 5, 632 (1955)]. Virginiamycin (Staphylomycine®) comprises mainly factor $M_1$ (VM1) combined with factor S (VS).

F. Le Goffic et. al., *Transformations of Pristinamycin II to Study Its Mechanism of Action,* 16(1) Eur. J. Medicinal Chemistry 69 (January–February 1981), have disclosed the preparation of dihydroxy derivatives of pristinamycin IIA.

Great Britain patent application GB-A-2 206 879 discloses modified group A streptogramin derivatives of structure:

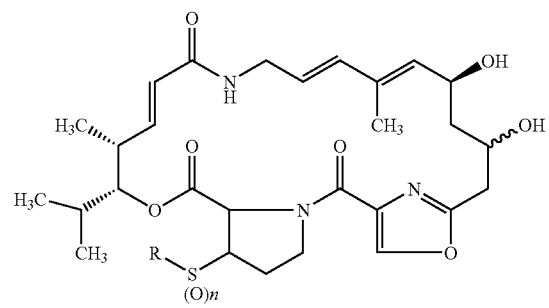

wherein:
R is a substituted alkyl radical or a heterocyclic radical and n is 1 or 2, however, these derivatives show no activity orally.

The inventors have now found that the group A streptogramin derivatives of formula (I):

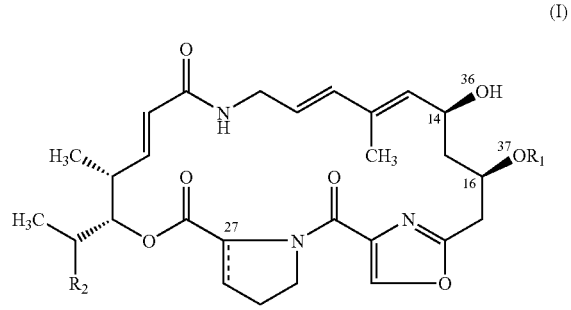

(I)

wherein:
$R_1$ is chosen from alkyl groups, alkenyl groups, alkynyl groups which may be mono- or polyfluoro groups, $C_3$–$C_6$ cycloalkyl groups, a phenylmethyl group, and heterocyclylmethyl groups, wherein said heterocyclyl portion is aromatic, $R_2$ is chosen from a hydrogen atom, a methyl group, and an ethyl group, the bond

----- is a single bond (27R stereochemistry) or a double bond,
unless otherwise stated, the alkyl groups are chosen from straight and branched $C_1$–$C_6$ alkyl groups,
unless otherwise stated, the alkenyl groups are chosen from straight and branched $C_3$–$C_6$ alkenyl groups, and
unless otherwise stated, the alkynyl groups are chosen from straight and branched $C_3$–$C_6$ alkynyl groups, have advantageous antibacterial activity, alone or when combined with at least one group B streptogramin derivative.

In one embodiment of the invention, for example, when $R_1$ is a heterocyclylmethyl group, the heterocyclyl portion can, for example, be chosen from a pyrrolyl group, a furyl group, a thienyl group, an imidazolyl group, and a pyridyl group.

In one embodiment of the invention, for example, when $R_1$ is chosen from alkyl groups mono- or polysubstituted with a fluorine atom, the alkyl groups can, for example, be chosen from $C_1$ and $C_2$ alkyl groups.

In another embodiment, for example, $R_1$ can be chosen from alkenyl groups, such as, an allyl group. In yet another embodiment, $R_1$ can be chosen from alkynyl groups, such as, for example, a propargyl group.

The streptogramin derivatives of formula (I) may be prepared, for example, by:
(a) reacting, in the presence of a phase-transfer agent, a derivative of formula (IIA):

$$R_1-X \qquad (IIa)$$

wherein:
$R_1$ is chosen from alkyl groups, alkenyl groups, alkynyl groups which may be mono- or polyfluoro groups, $C_3$–$C_6$ cycloalkyl groups, a phenylmethyl group, and heterocyclylmethyl groups, wherein said heterocyclyl portion is aromatic, and X is chosen from halogen atoms, a methylsulfonyloxy group, a p-toluenesulfonyloxy group, and a trifluoromethylsulfonyloxy group, with a dihydroxy streptogramin derivative of formula (II):

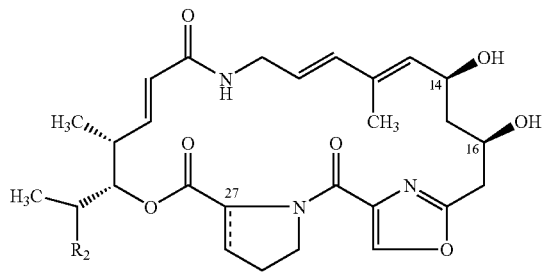

(II)

wherein:
R₂ is chosen from a hydrogen atom, a methyl group, and an ethyl group, the bond

- - - - - is a single bond (27R stereochemistry) or a double bond, and
(b) optionally protecting with a protecting group, prior to said reacting, the hydroxyl function in position 14, and then, where appropriate, removing said protecting group from position 14, and
(c) optionally protecting with a protecting group, prior to said reacting, the amide function in position 8, and then, where appropriate, removing said protecting group from position 8.

In one embodiment of the invention, for example, when X is chosen from halogen atoms, a derivative of formula (IIa), wherein X is chosen from a bromine atom and an iodine atom, can be used for said reacting.

The phase-transfer agent can, for example, be chosen from quaternary ammonium derivatives, for example, salts of tetraalkylammonium and salts of trialkylbenzylammonium, such as, chloride, bromide, and sulfate salts.

Said reacting can, for example, be carried out in a basic medium, such as, for example, a basic medium comprising at least one agent chosen from sodium hydroxide, potassium hydroxide, potassium carbonate, and cesium carbonate.

Said reacting can also, for example, be carried out in an aqueous-organic medium, such as, for example, an aqueous-organic medium comprising at least one agent chosen from hydrocarbons (for example, toluene), halogenated solvents (for example, dichloromethane), and esters (for example, ethyl acetate).

Said reacting can, for example, take place at a temperature ranging, for example, from 10° C. to 60° C., such as, for example, at about 20° C.

The process, for example, can also be performed in the presence of an excess of the derivative of formula (IIa).

The protection and deprotection of the hydroxyl radical in position 14 and of the amide radical in position 8 can be carried out according to known, art-recognized methods which do not affect the rest of the molecule, such as, for example, by applying the methods described by T. W. Greene and P. G. M. Wuts, Protective Groups in Organic Synthesis (2nd edition), A. Wiley—Interscience Publication (1991) or by McOmie, Protective Groups in Organic Chemistry, Plenum Press (1973). For example, the protection of the hydroxyl radical in position 14 can be carried out with an allyl protecting group which can be installed and removed by analogy with the methods described below in the examples. The protection of the amide in position 8 may, for example, be carried out with a t-butoxycarbonyl protecting group.

When the reaction leads to a mixture of the 14- and 16-O-alkyl isomers, these isomers may be separated according to known, art-recognized methods which do not affect the rest of the molecule, such as, for example, by chromatography, i.e., high performance liquid chromatography (HPLC) on a normal or reverse phase, on a chiral or non-chiral phase, or by flash chromatography, by crystallization, or by any other appropriate separation technique known in the art.

According to the invention, the streptogramin derivatives of formula (I) may also be prepared, for example, by a process comprising:
(a) desilylation of a silyl and 14-O-allyl derivative of formula (III):

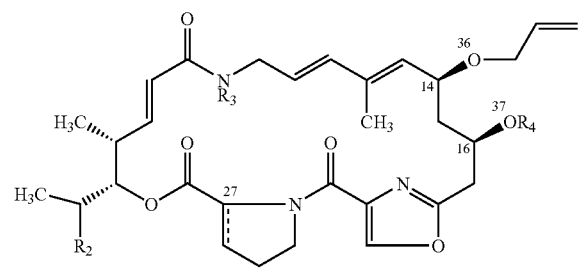

(III)

wherein:
R₂ is chosen from a hydrogen atom, a methyl group, and an ethyl group,
the bond

- - - - - is a single bond (27R stereochemistry) or a double bond,
R₃ is a protecting group, and
R₄ is a silyl group,
(b) 37-O-alkylation of the product obtained in (a) above, and
(c) removal of the 14-O-allyl group and the R₃ protecting group according to known methods which do not affect the rest of the molecule.

In one embodiment of the invention, the protecting group R₃ can, for example, be a t-butoxycarbonyl group.

Representative R₄ silyl groups include, for example, trialkylsilyl groups, dialkylphenylsilyl groups, and alkyldiphenylsilyl groups, for example, a t-butyldiphenylsilyl group and a t-butyldimethylsilyl group.

The desilylation, for example, can be carried out according to known, art-recognized methods which do not affect the rest of the molecule. The process can, for example, be performed in the presence of a source of fluoride ions, such as, for example, tetra-n-butylammonium fluoride or, for example, a hydrofluoric acid/amine complex, wherein the amine, for example, can be an amine chosen from triethylamine and pyridine. The reaction, for example, can be carried out in a chlorinated solvent (for example, dichloromethane) or in an ether (for example, tetrahydrofuran) at a temperature ranging, for example, from 20° C. to 80° C.

The 37-O-alkylation reaction, for example, can be carried out by reacting a derivative of formula (IIa) as defined above, with the desilylated streptogramin of formula (III). This process can be performed under an inert atmosphere (for example, under nitrogen or argon), in basic medium, for example, in the presence of sodium hydride, alkali metal (for example, lithium, sodium, or potassium) hexamethyldisilylamide, or in the presence of an organolithium reagent (for example, n-butyllithium), or alternatively in the presence of an amide (for example, lithium diisopropylamide), in an inert solvent such as an amide (for example, dimethylformamide) or an ether (for example, tetrahydrofuran), at a temperature ranging, for example, from −20° C. to 60° C.

Removal of the allyl group can be carried out, for example, in the presence of a proton donor such as 4-methylphenylsulphinic acid, in the presence of a palladium catalyst, for example, tetrakis(triphenylphosphine)-palladium, in a chlorinated solvent, for example, dichloromethane, at a temperature ranging, for example, from 0° C. to 60° C. It is also possible to perform the process according to the methods described in the references cited above. The t-butoxycarbonyl group can, for example, be removed according to known methods which do not affect the rest of the molecule, such as, for example, in a solvent such as dimethyl sulfoxide, dimethylformamide or diphenyl ether, at a temperature ranging, for example, from 130° C. to 170° C.

The streptogramin derivative of formula (III) may be prepared, for example, by 36-O-allylation and then 37-O-silylation and protection of the amide in position 8 with a radical $R_3$, and where appropriate optionally removing the protecting group $R_3$.

The 36-O-allylation can be carried out according to known, art-recognized methods, such as, for example, those cited in the above references. For example, the 36-O-allylation may be carried out by reacting an allyl halide (for example, bromide) or a methylsulfonyloxy derivative, p-toluenesulfonyloxy derivative, or a trifluoromethylsulfonyloxy derivative in the presence of a base, such as a carbonate (for example, potassium carbonate or cesium carbonate), in a solvent, such as a ketone (for example, methyl ethyl ketone), a nitrile (for example, acetonitrile) or a hydrocarbon (for example, toluene), at a temperature ranging, for example, from 40° C. to 80° C., such as, for example, about 70° C.

The silylation may be carried out, for example, according to known, art-recognized methods which do not affect the rest of the molecule, such as by using a halide (for example, a chloride) of the silyl group $R_4$. For example, the process can be performed using trialkylsilyl chloride, dialkylphenylsilyl chloride or alkyldiphenylsilyl chloride (for example, t-butyldiphenylsilyl chloride or t-butyldimethylsilyl chloride), working in a solvent, such as a chlorinated solvent (for example, dichloromethane), an amide (for example, dimethylformamide), an ether (for example, tetrahydrofuran), or a nitrile (for example, acetonitrile), at a temperature ranging, for example, from 0° C. to 60° C., such as, for example, at about room temperature.

The installation of the protecting group $R_3$ can be carried out, for example, according to the methods mentioned above. For example, it can be carried out in the presence of an excess of di-t-butyl dicarbonate, a base (triethylamine or pyridine) and optionally a catalyst, such as 4-dimethylaminopyridine, in a chlorinated solvent (dichloromethane) or an ether (tetrahydrofuran) at a temperature ranging, for example, from 0° C. to 80° C.

For example, the dihydroxylated group A streptogramin derivative of formula (II) may be obtained by:

(a) selective reduction of a natural pristinamycin component of formula (IV):

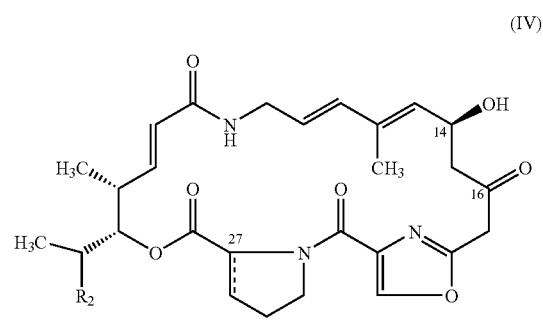

wherein:
$R_2$ is chosen from a hydrogen atom, a methyl group, and an ethyl group, and the bond

----- is a single bond (27R stereochemistry) or a double bond, and (b) separation of the 16S epimer form.

The reduction can be carried out, for example, in the presence of a reducing agent, such as an alkali metal borohydride, for example, sodium borohydride or sodium triacetoxyborohydride, in an organic solvent chosen from chlorinated solvents (for example, dichloromethane, dichloroethane or chloroform), tetrahydrofuran, acetic acid and alcohols such as methanol, ethanol or 2-propanol, at a temperature ranging, for example, from −78° C. to 40° C.

The separation of the 16R epimer form and of the 16S epimer form can be carried out, for example, according to known, art-recognized methods. For example, the separation of the epimer forms may be carried out by chromatography, flash chromatography, high performance liquid chromatography (HPLC), on a chiral or non-chiral phase, or centrifugal partition chromatography (CPC), starting with the mixture of the 16R and 16S epimers. Further, the separation may be carried out by crystallization, or by any other appropriate separation technique available in the art.

The pristinamycin derivatives of formula (IV) correspond, respectively, to pristinamycin IIA (PIIA), pristinamycin IIB (PIIB), pristinamycin IIC (PIIC), pristinamycin IID (PIID), pristinamycin IIF (PIIF), and pristinamycin IIG (PIIG), which are known components of natural pristinamycin. The components PIIF and PIIG have been disclosed in European patent application no. EP-A-0 614 910. Pristinamycin IIC (PIIC) and pristinamycin IID (PIID) may be obtained as described by J. C. Barriere et al., Expert. Opin. Invest. Drugs, 3(2), 115-31 (1994).

The present invention also relates to pristinamycin derivatives of formula (III), which are novel products.

The preparation and separation of the natural group A streptogramin components [streptogramins of formula (IV)] can be carried out, for example, by fermentation and isolation of the constituents from the fermentation must according to or by analogy with the method described by J. Preud'homme et al., Bull. Soc. Chim. Fr., vol. 2, 585 (1968), or in European patent application no. EP-A-0 614 910. Additionally, the preparation of natural group A components may be carried out, for example, by specific fermentation, as disclosed in French patent application no. FR-A-2 689 518.

The streptogramin derivatives of formula (I) may be purified, where appropriate, by physical methods such as crystallization, chromatography and Centrifugal Partition Chromatography (CPC).

The streptogramin derivatives according to the present invention have superior antibacterial properties and synergistic properties with respect to the antibacterial activity of the group B streptogramin derivatives. They are notably advantageous on account of their powerful activity, alone or in combination.

When at least one group A streptogramin derivative of the invention is combined with at least one group B streptogramin component or derivative, this component or derivative may be chosen, depending on whether it is desired to obtain a form for oral or parenteral administration, from natural group B streptogramin components, such as, for example, pristinamycin IA, pristinamycin IB, pristinamycin IC, pristinamycin ID, pristinamycin IE, pristinamycin IF, pristinamycin IG, virginiamycin S1, S3 or S4, vernamycin B or C, etamycin, and from semisynthetic derivatives as disclosed in U.S. Pat. Nos. or European patent application nos. U.S. Pat. Nos. 4,618,599, 4,798,827, 5,326,782, EP-A-0 772 630 and EP-A-0 770 132.

Representative group B streptogramin components and derivatives may include, for example, (I) streptogramin derivatives of formula (A), and salts thereof:

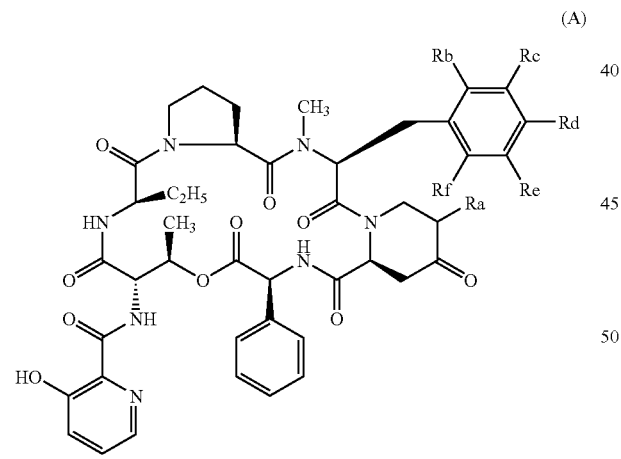

(A)

wherein:
(1) Rb, Rc, Re, and Rf are each a hydrogen atom; Rd is chosen from a hydrogen atom and a dimethylamino group; and
Ra is chosen from:
(A) —CH₂R'a groups, wherein R'a is chosen from:
(i) a pyrrolidinyl-3-thio group,
(ii) a piperidyl-3-thio group,
(iii) a piperidyl-4-thio group,
wherein said groups (i)–(iii) may be unsubstituted or substituted with at least one group chosen from alkyl groups, and (iv) alkylthio groups which are substituted with 1 or 2 groups chosen from:
(a) a hydroxysulfonyl group,
(b) alkylamino groups,
(c) dialkylamino groups, which may be unsubstituted or substituted with at least one group chosen from a mercapto group or dialkylamino groups,
(d) a piperazine ring which may be substituted or unsubstituted, a morpholino group, a thiomorpholino group, a piperidino group, a 1-pyrrolidinyl group, a 2-piperidyl group, a 3-piperidyl group, a 4-piperidyl group, a 2-pyrrolidinyl group, and a 3-pyrrolidinyl group, each of which may be unsubstituted or substituted with alkyl, and (B) =CHR'a groups, wherein R'a is chosen from:
(i) a pyrrolidinyl-3-amino group,
(ii) a piperidyl-3-amino group and a piperidyl-4-amino group,
(iii) a pyrrolidinyl-3-oxy group,
(iv) a piperidyl-3-oxy group and a piperidyl-4-oxy group,
(v) a pyrrolidinyl-3-thio group,
(vi) a piperidyl-3-thio group and a piperidyl-4-thio group, wherein said groups (i)–(vi) may be unsubstituted or substituted with at least one group chosen from alkyl groups,
(vii) alkylamino groups,
(viii) alkyloxy groups, and
(ix) alkylthio groups, wherein said groups (vii), (viii), and (ix) are substituted with 1 or 2 groups chosen from:
(a) a hydroxysulfonyl group,
(b) alkylamino groups,
(c) dialkylamino groups unsubstituted or substituted with at least one group chosen from dialkylamino groups,
(d) trialkylammonio groups,
(e) a 4-imidazolyl group, and a 5-imidazolyl group, each of which may be unsubstituted or substituted with alkyl,
(f) a piperazine ring which may be substituted or unsubstituted, a morpholino group, a thiomorpholino group, a piperidino group, a 1-pyrrolidinyl group, a 2-piperidyl group, a 3-piperidyl group, a 4-piperidyl group, a 2-pyrrolidinyl group, and a 3-pyrrolidinyl group, each of which may be unsubstituted or substituted with alkyl, (C) a quinuclidinyl-3-thiomethyl group, and
(D) a quinuclidinyl-4-thiomethyl group; or
(2) Ra is a hydrogen atom, and
(a) Rb, Re, and Rf are each a hydrogen atom, and Rd is chosen from a —NHCH₃ group and a —N(CH₃)₂ group, and Rc is chosen from a chlorine atom and a bromine atom, or, when Rd is a —N(CH₃)₂ group, Rc is chosen from (C₃–C₅) alkenyl groups, or
(b) Rb, Rd, Re, and Rf are each a hydrogen atom, and Rc is chosen from halogen atoms, aminomonoalkyl groups, aminodialkyl groups, alkyloxy groups, a trifluoromethyloxy group, thioalkyl groups, (C₁–C₃) alkyl groups, and trihalomethyl groups, or
(c) Rb, Rc, Re, and Rf are each a hydrogen atom, and Rd is chosen from halogen atoms, an ethylamino group, a diethylamino group, a methylethylamino group, alkyloxy groups, a trifluoromethyloxy group, thioalkyl groups, ($C_1$–$C_6$) alkyl groups, aryl groups, and trihalomethyl groups, or (d) Rb, Re, and Rf are each a hydrogen atom, Rc is chosen from halogen atoms, aminomonoalkyl groups, aminodialkyl groups, alkyloxy groups, a trifluoromethyloxy group, thioalkyl groups, and ($C_1$–$C_3$) alkyl groups, and Rd is chosen from halogen atoms, an amino group, aminomonoalkyl groups, aminodialkyl groups, alkyloxy groups, a trifluoromethyloxy group, thioalkyl groups, ($C_1$–$C_6$) alkyl groups, and trihalomethyl groups, or (e) Rc, Re, and Rf are each a hydrogen atom, and Rb and Rd are each a methyl group, and further, for example, (II) semisynthetic group B streptogramin derivatives of formula (B), and salts thereof:

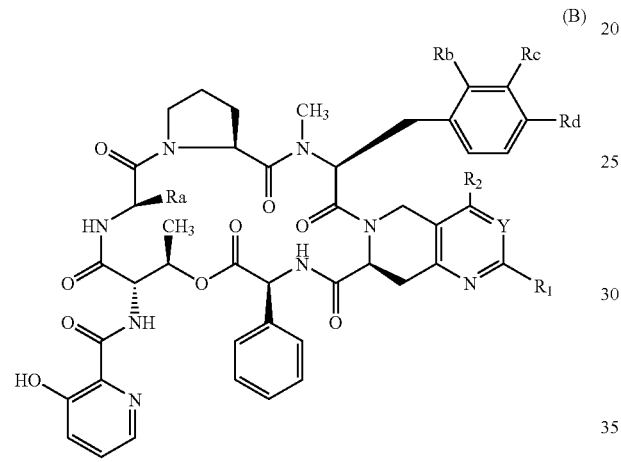

(B)

wherein:

(A) Y is chosen from (i) a nitrogen atom and (ii) =$CR_3$— groups, and (1) when Y is chosen from =$CR_3$— groups, $R_1$ is chosen from ($a_1$) a hydrogen atom, $C_1$–$C_8$ alkyl groups, and $C_2$–$C_8$ alkenyl groups, ($b_1$) $C_3$–$C_8$ cycloalkyl groups, and saturated and unsaturated 3- to 8-membered heterocyclyl groups, ($c_1$) an unsubstituted phenyl group, ($d_1$) a phenyl group substituted with at least one substituent chosen from halogen atoms, a hydroxyl group, alkyl groups, alkyloxy groups, alkylthio groups, alkylsulfinyl groups, alkylsulfonyl groups, an amino group, alkylamino groups, and dialkylamino groups, and ($e_1$) groups —NR'R", wherein:

R' and R", which are identical or different, are each chosen from a hydrogen atom, and $C_1$–$C_3$ alkyl groups, or R' and R", form, together with the nitrogen atom to which they are attached, a 3- to 8-membered heterocyclyl group, wherein one of said members, in addition to said nitrogen atom, may be a heteroatom chosen from an oxygen atom, a sulfur atom, and a nitrogen atom, and wherein said heterocyclyl group is unsubstituted or substituted with a group chosen from alkyl groups, $C_2$–$C_8$ alkenyl groups, $C_3$–$C_6$ cycloalkyl groups, saturated and unsaturated 4- to 6-membered heterocyclyl groups, a benzyl group, an unsubstituted phenyl group, and a substituted phenyl group, as defined above in ($d_1$), ($f_1$) halomethyl groups, a hydroxymethyl group, and alkyloxymethyl groups, ($g_1$) alkylthiomethyl groups, wherein said alkyl portion is unsubstituted or substituted with an —NR'R" group, and wherein said R' and said R" are as defined above in ($e_1$), ($h_1$) alkylsulfinylmethyl groups, alkylsulfonylmethyl groups, an acyloxymethyl group, a benzoyloxymethyl group, a cyclopropylaminomethyl group, and —($CH_2$)$_n$NR'R" groups, wherein n is chosen from integers ranging from 1 to 4, and wherein said R' and said R" are as defined above in ($e_1$), and ($i_1$) when $R_3$ is a hydrogen atom, $R_1$ is additionally chosen from a formyl group, a carboxyl group, alkyloxycarbonyl groups, and —CONR'R" groups, wherein said R' and said R" are defined as above in ($e_1$), and (2) when Y is a nitrogen atom, $R_1$ is chosen from ($a_2$) options ($a_1$), ($b_1$), ($c_1$), ($d_1$), and ($e_1$) as defined above, and ($b_2$) XR° groups, wherein X is chosen from an oxygen atom, a sulfur atom, a sulfinyl group, a sulfonyl group, and an —NH— group, and wherein R° is chosen from (i) ($C_1$ to $C_8$) alkyl groups, (ii) ($C_3$ to $C_6$) cycloalkyl groups, (iii) saturated and unsaturated 3- to 8-membered heterocyclyl groups, (iv) 3- to 8-membered heterocyclylmethyl groups in which the heterocyclyl portion is attached to the methyl group by a carbon atom, (v) an unsubstituted phenyl group, (vi) phenyl groups substituted with at least one group chosen from halogen atoms, a hydroxyl group, alkyl groups, alkyloxy groups, alkylthio groups, alkylsulfinyl groups, alkylsulfonyl groups, an amino group, alkylamino groups, and dialkylamino groups, (vii) —($CH_2$)$_n$NR'R" groups, wherein R' and R" are as defined above in ($e_1$), and wherein n is chosen from integers ranging from 2 to 4, and (viii) if X is an NH group, R° may also be a hydrogen atom;

(B) $R_2$ is chosen from a hydrogen atom and $C_1$–$C_3$ alkyl groups, (C) $R_3$ is chosen from a hydrogen atom, alkyl groups, a carboxyl group, alkyloxycarbonyl groups, and carbamoyl groups of formula —CO—NR'R", wherein said R' and said R" are defined as above in ($e_1$), (D) Ra is chosen from a methyl group and an ethyl group, and (E) Rb, Rc, and Rd are defined as follows:

(1) Rb and Rc are each a hydrogen atom and

Rd is chosen from a hydrogen atom, a methylamino group, and a dimethylamino group, or (2) Rb is a hydrogen atom, Rc is chosen from a hydrogen atom, a chlorine atom, a bromine atom, and $C_3$–$C_5$ alkenyl groups, and Rd is chosen from —N($CH_3$)R''' groups, wherein R''' is chosen from (a) alkyl groups, (b) $C_2$–$C_4$ hydroxyalkyl groups, (c) $C_2$–$C_8$ alkenyl groups, wherein said $C_2$–$C_8$ alkenyl groups are unsubstituted or substituted with (i) an unsubstituted phenyl group, (ii) a cycloalkyl ($C_3$–$C_6$)methyl group, (iii) an unsubstituted benzyl group, (iv) a benzyl group substituted with at least one substituent chosen from halogen atoms, a hydroxyl group, alkyl groups, alkyloxy groups, alkylthio groups, alkylsulfinyl groups, alkylsulfonyl groups, an amino group, alkylamino groups, and dialkylamino groups, or (v) heterocyclylmethyl groups and heterocyclylethyl groups, wherein said heterocyclyl portions of said heterocyclylmethyl groups and said heterocyclylethyl groups are chosen from saturated and unsaturated 5- to 6-membered heterocyclyl groups comprising from 1 to 2 heteroatoms chosen from a sulfur atom, an oxygen atom, and a nitrogen atom, and wherein said heterocyclyl groups may be unsubstituted or substituted with a group chosen from alkyl groups, $C_2$–$C_8$ alkenyl groups, $C_3$–$C_6$ cycloalkyl groups, saturated and unsaturated 4- to 6-membered heterocyclyl groups, an unsubstituted phenyl group, a benzyl group, or a substituted phenyl group as defined above in ($d_1$), (d) a cyanomethyl group, (e) —CH$_2$CORe groups, wherein Re is chosen from
  (i) —OR'e groups, wherein R'e is chosen from a hydrogen atom, $C_1$–$C_6$ alkyl groups, $C_2$–$C_6$ alkenyl groups, a benzyl group, and heterocyclylmethyl groups, wherein said heterocyclyl portion is chosen from 5- to 6-membered heterocyclyl groups comprising from 1 to 2 heteroatoms chosen from a sulfur atom, an oxygen atom, and a nitrogen atom, (ii) alkylamino groups, alkylmethylamino groups, heterocyclylamino groups and heterocyclylmethylamino groups, wherein said heterocyclyl portion of said heterocyclylamino groups and said heterocyclylmethylamino groups is chosen from 5- to 6-membered saturated heterocyclyl groups comprising from 1 to 2 heteroatoms chosen from a sulfur atom, an oxygen atom, and a nitrogen atom, and wherein said heterocyclyl groups may be unsubstituted or substituted with a group chosen from alkyl groups, a benzyl group, and alkyloxycarbonyl groups, or (3) Rb is a hydrogen atom,
Rd is chosen from an —NHCH$_3$ group and an —N(CH$_3$)$_2$ group, and
Rc is chosen from a chlorine atom, and a bromine atom, and when Rd is an —N(CH$_3$)$_2$ group, Rc is chosen from $C_3$–$C_5$ alkenyl groups, or (4) Rb and Rd are each a hydrogen atom, and
Rc is chosen from halogen atoms, alkylamino groups, dialkylamino groups, alkyloxy groups, a trifluoromethoxy group, thioalkyl groups, $C_1$–$C_6$ alkyl groups, and trihalomethyl groups, or (5) Rb and Rc are each a hydrogen atom, and
Rd is chosen from halogen atoms, an ethylamino group, a diethylamino group, a methylethylamino group, alkyloxy groups, a trifluoromethoxy group, alkylthio groups, alkylsulfinyl groups, alkylsulfonyl groups, $C_1$–$C_6$ alkyl groups, a phenyl group, and trihalomethyl groups, or (6) Rb is a hydrogen atom, and
Rc is chosen from halogen atoms, alkylamino groups, dialkylamino groups, alkyloxy groups, a trifluoromethoxy group, thioalkyl groups, and $C_1$–$C_3$ alkyl groups, and
Rd is chosen from halogen atoms, an amino group, alkylamino groups, dialkylamino groups, alkyloxy groups, a trifluoromethoxy group, thioalkyl groups, $C_1$–$C_6$ alkyl groups, and trihalomethyl groups, or (7) Rc is a hydrogen atom, and
Rb and Rd are each a methyl group, and even further, for example, (III) semisynthetic group B derivatives of formula (C), and salts thereof, when salts exists:

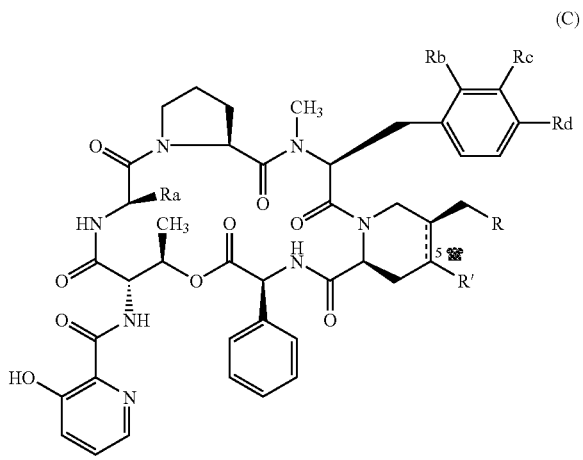

(C)

wherein:
(A) R is chosen from
  (1) —NR$_1$R$_2$ groups, wherein R$_1$ and R$_2$, which may be identical or different, are each chosen from
    (i) a hydrogen atom,
    (ii) ($C_1$–$C_8$) alkyl groups,
    (iii) ($C_1$–$C_8$) alkyl groups substituted with a hydroxyl group,
    (iv) ($C_3$–$C_8$) alkenyl groups,
    (v) ($C_3$–$C_8$) cycloalkyl groups,
    (vi) ($C_1$–$C_8$) alkyloxy groups,
    (vii) dialkylamino groups,
    (viii) phenylalkyl groups,
    (ix) phenylalkyl groups substituted with at least one group chosen from halogen atoms, alkyl groups, hydroxyalkyl groups, alkyloxy groups, and dialkylamino groups, and
    (x) 3- to 8-membered saturated and unsaturated heterocyclylalkyl groups comprising at least one hetero atom chosen from nitrogen, oxygen, and sulfur, or
    (xi) R$_1$ and R$_2$ form, together with the nitrogen atom to which they are attached, a saturated, partially saturated or unsaturated mono- or polycyclic 3- to 12-membered heterocycle group, wherein one of said members, in addition to said nitrogen atom, may be an atom chosen from oxygen, sulfur, and nitrogen, and wherein said heterocyclyl group is unsubstituted or substituted with at least one group chosen from a hydroxyl group, alkyl groups, an unsubstituted phenyl group, a phenyl group substituted with a halogen atom, phenylalkyl groups, phenyl($C_2$–$C_4$)alkenyl groups, hydroxyalkyl groups, acyl groups, alkyloxycarbonyl groups, heterocyclyl groups and heterocyclylcarbonyl groups, wherein the heterocyclyl portion is saturated or unsaturated (4- to 6-membered) and comprises at least one hetero atom chosen from nitrogen, sulfur, and oxygen, and
  (2) —SR$_3$ groups, wherein R$_3$ is chosen from
    (i) ($C_1$–$C_8$) alkyl groups and ($C_3$–$C_8$) cycloalkyl groups substituted with —NR$_1$R$_2$, wherein R$_1$ and R$_2$, which may be identical or different, are each chosen from a hydrogen atom and alkyl groups, or form, together with the nitrogen atom to which they are attached, a heterocycle as defined in (xi) above, and (ii) saturated and unsaturated heterocyclyl and heterocyclylmethyl (3- to 7-membered) groups, wherein one of said members, in addition to said nitrogen atom, may be an atom chosen from oxygen, sulfur, and nitrogen, and wherein said heterocyclyl portion is unsubstituted or substituted with an alkyl group,

is a residue of an unsaturated ring which is not substituted in the 5γ position

or the residue of a saturated ring which is substituted in the 5γ position with a fluorine atom

(C) Ra is chosen from a methyl group and an ethyl group, and (D) Rb, Rc and Rd are defined below:

1) Rb and Rc are each a hydrogen atom, and Rd is chosen from a hydrogen atom, a methylamino group, and a dimethylamino group, or 2) Rb is a hydrogen atom,
Rc is chosen from a hydrogen atom, a chlorine atom, a bromine atom, and a ($C_3$ to $C_5$) alkenyl group, and
Rd is —N(CH$_3$)—R''', wherein R''' is chosen from:
(1) alkyl groups, (2) ($C_2$ to $C_4$) hydroxyalkyl groups, (3) ($C_2$ to $C_8$) alkenyl groups, (4) phenylalkenyl groups, (5) cycloalkyl($C_3$ to $C_6$)methyl groups, (6) an unsubstituted benzyl group, (7) a substituted benzyl group, (8) heterocyclylmethyl groups and heterocyclylethyl groups, (9) a —CH$_2$CN group, (10) a —CH$_2$COOH group, and (11) —CORe groups and —CH$_2$CORe groups for which either:
(a) Re is —OR'e, wherein R'e is chosen from a hydrogen atom, $C_1$–$C_6$ alkyl groups, $C_2$–$C_6$ alkenyl groups, a benzyl group, and heterocyclylmethyl groups, wherein said heterocyclyl portion is chosen from 5- to 6-membered heterocyclyl groups comprising from 1 to 2 heteroatoms chosen from a sulfur atom, an oxygen atom, and a nitrogen atom, or
(b) Re is chosen from alkylamino groups, alkylmethylamino groups, heterocyclylamino groups, and heterocyclylmethylamino groups, or 3) Rb is a hydrogen atom,
Rd is chosen from an —NHCH$_3$ group and an —N(CH$_3$)$_2$ group, and Rc is chosen from a chlorine atom, and a bromine atom, and when Rd is an —N(CH$_3$)$_2$ group, Rc is chosen from $C_3$–$C_5$ alkenyl groups, or 4) Rb and Rd are each a hydrogen atom, and
Rc is chosen from halogen atoms, alkylamino groups, dialkylamino groups, alkyloxy groups, a trifluoromethoxy group, thioalkyl groups, ($C_1$–$C_6$) alkyl groups, and trihalomethyl groups, or 5) Rb and Rc are each a hydrogen atom, and
Rd is chosen from halogen atoms, an ethylamino group, a diethylamino group, a methylethylamino group, alkyloxy groups, a trifluoromethoxy group, alkylthio groups, alkylsulfinyl groups, alkylsulfonyl groups, ($C_1$–$C_6$) alkyl groups, a phenyl group, and trihalomethyl groups, or 6) Rb is a hydrogen atom,
Rc is chosen from halogen atoms, alkylamino groups, dialkylamino groups, alkyloxy groups, a trifluoromethoxy group, thioalkyl groups, ($C_1$–$C_3$) alkyl groups, and
Rd is chosen from halogen atoms, an amino group, alkylamino groups, dialkylamino groups, alkyloxy groups, a trifluoromethoxy group, thioalkyl groups, ($C_1$–$C_6$) alkyl groups, and trihalomethyl groups, or 7) Rc is a hydrogen atom, and
Rb and Rd are each a methyl group.

It is understood that the combinations formed from the derivatives according to the invention and from group B streptogramins also fall within the context of the present invention.

The group B streptogramin derivatives of formula (B) may be prepared, for example, according to the methods disclosed in International patent application no. PCT/FR 99/00409. The group B streptogramin derivatives of formula (C) may be prepared, for example, according to the methods disclosed in International patent application no. PCT/FR 00/02146.

In vitro on *Staphylococcus aureus* IP8203, the streptogramin derivatives according to the invention have been shown to be active at concentrations ranging, for example, from 0.06 to 32 μg/ml, alone or combined with at least one group B derivative such as pristinamycin IB. In vivo, the streptogramin derivatives according to the invention synergized the antimicrobial activity of pristinamycin IB on experimental infections of mice with *Staphylococcus aureus* IP8203 at doses; ranging, for example, from 32 to 150 mg/kg orally (DC$_{50}$).

Representative streptogramin derivatives of formula (I) include, for example, streptogramin derivatives of formula (I) wherein:
R$_1$ is chosen from alkyl groups, alkenyl groups, and alkynyl groups,
R$_2$ is a methyl group, and
the bond ----- is a single bond (27R stereochemistry) or al double bond. The compounds described below in the Examples are exemplary of such products.

The compounds according to the invention are advantageous on account of their low toxicity. None of the compounds of the invention has shown any toxicity at doses of 150 mg/kg on Staphylococcus aureus IP8203, when administered twice a day subcutaneously or orally in mice.

Representative group A streptogramin derivatives of formula (I), which may be used according to the invention, for example, include the compounds mentioned below in the examples, and the following compounds:
(16R)-16-deoxo-16-trifluoromethoxypristinamycin II$_B$
(16R)-16-deoxo-16-trifluoromethoxypristinamycin II$_A$ (16R)-16-deoxo-16-difluoromethoxypristinamycin II$_B$
(16R)-16-deoxo-16-difluoromethoxypristinamycin II$_A$
(16R)-16-deoxo-16-fluoromethoxypristinamycin II$_B$
(16R)-16-deoxo-16-fluoromethoxypristinamycin II$_A$
(16R)-16-deoxo-16-cyclopropyloxypristinamycin II$_B$
(16R)-16-deoxo-16-cyclopropyloxypristinamycin II$_A$
(16R)-16-deoxo-16-cyclobutyloxypristinamycin II$_B$
(16R)-16-deoxo-16-cyclobutyloxypristinamycin II$_A$
(16R)-16-deoxo-16-isopropyloxypristinamycin II$_B$
(16R)-16-deoxo-16-isopropyloxypristinamycin II$_A$
(16R)-16-deoxo-16-(2-fluoropropen-3-yloxy)pristinamycin II$_B$
(16R)-16-deoxo-16-(2-fluoropropen-3-yloxy)pristinamycin II$_A$.

The examples which follow, given without any implied limitation, illustrate the present invention.

In the examples which follow, the 16-deoxopristinamycin IIA (or IIB) nomenclature indicates the replacement of the ketone function in position 16 with 2 hydrogen atoms. As the chromatography proceeded, all the fractions were analyzed by thin layer chromatography (TLC) on Merck 60F254 silica plates. The fractions corresponding to the same spot on TLC were combined and then concentrated to dryness, under reduced pressure (30° C.; 2.7 kPa). The residues thus obtained were analyzed by known, art-recognized spectroscopic techniques (NMR; IR; MS), allowing the expected product to be identified.

EXAMPLE 1

(16R)-16-Deoxo-16-methoxypristinamycin II$_B$

A solution of 0.6 g of (16R)-8-N-tert-butyloxycarbonyl-16-deoxo-16-methoxypristinamycin II$_B$ in 15 cm$^3$ of N,N-dimethylformamide was boiled for 2.5 hours. The reaction mixture was poured into 200 cm$^3$ of ice-cold water and the aqueous phase was then extracted with 3 times 100 cm$^3$ of ethyl acetate. The organic phases were combined, washed with 3 times 200 cm$^3$ of saturated aqueous sodium chloride solution, dried over magnesium sulfate, filtered and then concentrated to dryness under reduced pressure (2.7 kPa) to give 0.65 g of a yellow oil, which was purified by flash chromatography on silica [eluent: dichloromethane/methanol/acetonitrile (90/5/5 by volume)]. After concentrating the fractions containing the expected product, 0.16 g of a yellow foam was obtained and was recrystallized from 3 cm$^3$ of hot acetonitrile to give 0.13 g of (16R)-16-deoxo-16-methoxypristinamycin II$_B$, in the form of a white powder that melted at about 124° C. (dec.).

$^1$H NMR spectrum (400 MHz, CDCl$_3$, δ in ppm): 0.96 (d, J=6.5 Hz: 3H); 1.00 (d, J=6.5 Hz: 3H); 1.08 (d, J=6.5 Hz: 3H); 1.70 (ddd, J=14–7 and 3 Hz: 1H); from 1.75 to 2.05 (mt: 5H); 1.82 (s: 3H); 1.89 (d, J=3 Hz: 1H); 2.14 (mt: 1H); 2.75 (mt: 1H); 2.80 (dd, J=16 and 8.5 Hz: 1H); 3.18 (dd, J=16 and 3.5 Hz: 1H); 3.45 (s: 3H); 3.50 (mt: 1H); 3.75 (mt: 1H); 3.95 (mt: 2H); 4.45 (mt: 1H); 4.70 (mt: 1H); from 4.75 to 4.85 (mt: 2H); 5.37 (broad d, J=9 Hz: 1H); 5.72 (ddd, J=16–8 and 4.5 Hz: 1H); 5.81 (dd, J=16.5 and 1.5 Hz: 1H); 6.07 (mt: 1 H); 6.18 (d, J=16 Hz: 1H); 6.51 (dd, J=16.5 and 5 Hz: 1H); 8.10 (s: 1H).

(16R)-8-N-tert-Butyloxycarbonyl-16-deoxo-16-methoxypristinamycin II$_B$ was prepared in the following way:

2.4 cm$^3$ of 1N hydrochloric acid were added, at 0° C. under an argon atmosphere, to a solution of 0.41 g of sodium p-toluenesulfinate in 14 cm$^3$ of dichloromethane, and the mixture was then allowed to warm to room temperature over 15 minutes. This solution was dried over magnesium sulfate, filtered and then poured at 20° C., under an argon atmosphere, into a solution of 0.93 g of (16R)-14-O-allyl-8-N-tert-butyloxycarbonyl-16-deoxo-16-methoxypristinamycin II$_B$ and 0.31 g of tetrakis(triphenylphosphine)palladium in 18 cm$^3$ of dichloromethane. After stirring for 30 minutes at room temperature, the reaction mixture was poured into 100 cm$^3$ of water and the phases were then separated by settling. The organic phase was dried over magnesium sulfate, filtered and then concentrated to dryness; under reduced pressure (2.7 kPa) to give 1.66 g of a yellow oil which was purified by flash chromatography on silica [eluent: dichloromethane/acetonitrile/methanol (95/2.5/2.5 by volume)]. After concentrating the fractions containing the expected product, 0.63 g of a yellow foam was obtained and was stirred in 5 cm$^3$ of pentane and then filtered and dried under reduced pressure (2.7 kPa) to give 0.6 g of (16R)-8-N-tert-butyloxycarbonyl-16-deoxo-16-methoxypristinamycin II$_B$ in the form of a pale yellow solid.

$^1$H NMR spectrum (400 MHz, CDCl$_3$, δ in ppm): 0.96 (mt: 6H); 1.15 (d, J=6.5 Hz: 3H); from 1.35 to 2.15 (mt: 7H); 1.57 (s: 9H); 1.81 (s, 3H); 2.41 (d, J=2.5 Hz: 1H); 2.77 (mt: 1H); 2.87 (dd, J=16 and 8 Hz: 1H); 3.21 (dd, J=16 and 4 Hz: 1H); 3.46 (s: 3H); from 3.70 to 3.95 (mt: 3H); 4.12 (broad dd, J=14 and 4.5 Hz: 1H); 4.62 (dd, J=14 and 9 Hz: 1H); 4.72 (mt: 1H); 4.81 (dd, J=8 and 2.5 Hz: 1H); 4.89 (dd, J=10 and 2 Hz: 1H); 5.52 (broad d, J=9 Hz: 1H); 5.67 (ddd, J=16–9 and 4.5 Hz: 1H); 6.28 (d, J=16 Hz: 1H); 6.94 (dd, J=16 and 1.5 Hz: 1H); 7.04 (dd, J=16 and 4 Hz: 1H); 8.14 (s: 1H).

(16R)-14-O-Allyl-8-N-tert-butyloxycarbonyl-16-deoxo-16-methoxypristinamycin II$_B$ was prepared in the following way:

0.19 cm$^3$ of iodomethane and 0.043 g of 50% sodium hydride in petroleum jelly were added, at 25° C. under an argon atmosphere, to 0.4 g of (16R)-14-O-allyl-8-N-tert-butyloxycarbony 16-deoxo-16-hydroxy-pristinamyc in II$_B$ dissolved in 5 cm$^3$ of N,N-dimethylformamide. After stirring for 4 hours, the reaction mixture was diluted with 20 cm$^3$ of ethyl acetate and then poured into 40 cm$^3$ of water. The organic phase was separated out after settling had taken place, and then washed with 40 cm$^3$ of saturated aqueous sodium chloride solution, dried over magnesium sulfate, filtered and then concentrated to dryness under reduced pressure (2.7 kPa) to give 0.31 g of a yellow oil, which was purified by flash chromatography on silica [eluent: dichloromethane/acetonitrile/methanol (95/2.5/2.5 by volume)]. After concentrating the fractions containing the expected product, 0.06 g of (16R)-14-O-allyl-8-N-tert-butyloxycarbonyl-16-deoxo-16-methoxy-pristinamyc in II$_B$ was obtained in the form of a white solid.

$^1$H NMR spectrum (400 MHz, CDCl$_3$, δ in ppm): 0.96 (d, J=6.5 Hz: 6H); 1.15 (d, J=6.5 Hz: 3H); from 1.40 to 2.15 (mt: 7H); 1.57 (s: 9H); 1.82 (s, 3H); 2.78 (mt: 1H); 2.96 (dd, J=16 and 6 Hz: 1H); 3.06 (dd, J=16 and 4 Hz: 1H); 3.38 (s: 3H); from 3.70 to 3.85 (mt: 2H); 3.90 (mt: 2H); 3.98 (broad dd, J=12 and 5 Hz: 1H); 4.21 (dd, J=15 and 4 Hz: 1H); 4.37 (mt: 1H); 4.60 (dd, J=15 and 8.5 Hz: 1H); 4.84 (dd, J=8 and 2.5 Hz: 1H); 4.89 (dd, J=10 and 2 Hz: 1H); 5.15 (dd, J=10 and 1 Hz: 1H); 5.24 (dd, J=18 and 1 Hz: 1H); 5.35 (broad d, J=9 Hz: 1H); 5.70 (ddd, J=16–8.5 and 4 Hz: 1H); 5.89 (mt: 1H); 6.28 (d, J=16 Hz: 1 H); 6.98 (d, J=16 Hz: 1H); 7.04 (dd, J=16 and 4 Hz: 1H); 8.15 (s: 1H).

(16R)-14-O-Allyl-8-N-tert-butyloxycarbonyl-16-decoxo-16-hydroxypristinamycin II$_B$ was prepared in the following way:

90 cm$^3$ of triethylamine trihydrofluoride were added to 16.05 g of (16R)-14-O-allyl-16-(tert-butyl-dimethylsilyloxy-8-N-tert-butyloxycarbonyl-16-deoxo-pristinamycin II$_B$ dissolved in 80 cm$^3$ of dichloromethane. After stirring for 17 hours at 40° C., the reaction mixture was diluted with 100 cm$^3$ of dichloromethane and then poured into 300 cm$^3$ of water. The pH of the aqueous phase was adjusted to 8 by slow addition of sodium bicarbonate. The organic phase was separated out after settling had taken place and then dried over sodium sulfate, filtered and concentrated to dryness under reduced pressure (2.7 kPa) to give 16.5 g of a yellow oil, which was purified by flash chromatography on silica [eluent: dichloromethane/acetonitrile/methanol (93/3.5/3.5 by volume)]. After concentrating the fractions containing the expected products, 10.23 g of (16R)-14-O-allyl-8-N-tert-butyloxycarbonyl-16-deoxo-16-hydroxypristinamycin II$_B$ were obtained in the form of a yellow foam.

$^1$H NMR spectrum (400 MHz, CDCl$_3$, δ in ppm): 0.96 (mt: 6H); 1.15 (d, J=6.5 Hz: 3H); 1.43 (s, 9H); from 1.35 to 2.15 (mt: 6H); 1.78 (s: 3H); 2.27 (d mt, J=15 Hz: 1H); 2.77 (mt: 1H); 2.83 (dd, J=16 and 8 Hz: 1H); 3.05 (dd, J=16 and 5.5 Hz: 1H); 3.55 (d, J=1.5 Hz: 1H); from 3.70 to 3.95 (mt: 3H); 4.06 (broad dd, J=12 and 5 Hz: 1H); 4.15 (dd, J—14.5 and 4 Hz: 1H); 4.31 (mt: 1H); 4.53 (doubled t, J=9 and 4 Hz: 1H); 4.63 (dd, J=14.5 and 9 Hz: 1H); 4.86 (dd, J=8 and 2.5 Hz: 1H); 4.91 (dd, J=10 and 2 Hz: 1H); 5.19 (dd, J =10 and 1 Hz: 1H); 5.25 (dd, J=17.5 and 1 Hz: 1H); 5.42 (broad d, J=9 Hz: 1H); 5.66 (ddd, J=16–9 and 4 Hz: 1H); 5.91 (mt: 1H); 6.31 (d, J=16 Hz: 1H); 6.92 (d, J=16 Hz: 1H); 7.02 (dd, J=16 and 4 Hz: 1H); 8.14 (s: 1H).

(16R)-14-O-Allyl-16-(tert-butyldimethylsilyloxy)-8-N-tert-butyloxycarbonyl-16-deoxo-pristinamycin II$_B$ was prepared in the following manner:

0.20 cm$^3$ of triethylamine and 0.12 g of 4-N,N-dimethylaminopyridine were added to a solution of 1 g of (16R)-14-O-allyl-16-(tert-butyldimethylsilyloxy)-16-deoxopristinamycin II$_B$ and 3.4 g of di-tert-butyl dicarbonate in 30 cm$^3$ of dichloromethane, at 25° C. The reaction mixture was stirred for 16 hours at room temperature, diluted with 30 cm$^3$ of dichloromethane and then poured into 60 cm$^3$ of saturated aqueous sodium chloride solution. The organic phase was separated out after settling had taken place, dried over magnesium sulfate and concentrated to dryness under reduced pressure (2.7 kPa) to give 1.65 g of a yellow oil, which was purified by flash chromatography on silica [eluent: cyclohexane/ethyl acetate (60/40 by volume)]. After concentrating the fractions containing the expected product, 0.71 g of (16R)-14-O-allyl-16-(tert-butyldimethylsilyloxy)-8-N-tert-butyloxycarbonyl-16-deoxopristinamycin II$_B$ were obtained in the form of a thick pale yellow oil.

$^1$H NMR spectrum (400 MHz, CDCl$_3$, δ in ppm): 0.10 (s, 6H); 0.92 (s: 9H); 0.96 (mt: 6H); 1.15 (d, J=6.5 Hz: 3H); 1.43 (s: 9H); from 1.50 to 2.10 (mt: 7H); 1.83 (s: 3H); 2.77 (mt: 1H); 2.93 (dd, J=14.5 and 5 Hz: 1H); 2.99 (dd, J=14.5 and 3 Hz: 1H) ; 3.77 (broad dd, J=13 and 6 Hz: 1H); 3.90 (mt: 2H); 3.99 (broad dd, J=13 and 5 Hz: 1H); 4.12 (mt: 1H); from 4.25 to 4.35 (mt: 2H); 4.65 (mt: 1H); 4.83 (dd, J=8 and 2.5 Hz: 1H); 4.89 (dd, J=10 and 2 Hz: 1H); 5.14 (dd, J=10 and 1.5 Hz: 1H); 5.25 (dd, J=18 and 1.5 Hz: 1H); 539 (broad d, J=9 Hz: 1H), 5.68 (ddd, J=16–9 and 4.5 Hz: 1H); 5.89 (mt: 1H); 6.32 (d, J=16 Hz: 1H); 6.99 (d, J=16 Hz: 1H); 7.06 (dd, J=16 and 4 Hz: 1H); 8.16 (s: 1H).

(16R)-14-O-Allyl-16-(tert-butyldimethylsilyloxy)-16-deoxopristinamycin II$_B$ was prepared in the following manner:

3.06 cm$^3$ of diisopropylethylamine and 0.43 g of 4-N,N-dimethylaminopyridine were added, at 20° C. and under an argon atmosphere, to a solution of 2 g of (16R)-14-O-allyl-16-deoxo-16-hydroxypristinamycin II$_B$ and 2.64 g of tert-butyldimethylchlorosilane in 15 cm$^3$ of dichloromethane. After stirring for 17 hours, the reaction mixture was diluted with 50 cm$^3$ of dichloromethane and then poured into 50 cm$^3$ of saturated aqueous sodium chloride solution. The organic phase was separated out after settling had taken place, dried over magnesium sulfate, filtered and then concentrated to dryness under reduced pressure (2.7 kPa) to give a residue which was stirred for 2 hours in 30 cm$^3$ of diisopropyl ether. After filtering and drying under reduced pressure (2.7 kPa), 1.57 g of (16R)-14-O-allyl-16-(tert-butyldimethylsilyloxy)-16-deoxopristinamycin II$_B$ were obtained in the form of a white powder.

$^1$H NMR spectrum (400 MHz, CDCl$_3$, δ in ppm): 0.10 (s, 6H); 0.89 (s, 9H); 0.96 (d, J=6.5 Hz: 3H); 1.00 (d, J=6.5 Hz: 3H); 1.06 (d, J=6.5 Hz: 3H); 1.60 (mt: 1H); from 1.75 to 2.05 (mt: 5H); 1.82 (s: 3H); 2.16 (mt: 1H); 2.75 (mt: 1H); 2.88 (dd, J=16 and 7.5 Hz: 1H); 2.95 (dd, J=16 and 4 Hz: 1H); 3.47 (mt: 1H); 3.79 (dd, J=12 and 6 Hz: 1H); from 3.90 to 4.05 (mt: 3H); 4.13 (mt: 1H); 4.25 (mt: 1H); 4.50 (mt: 1H); from 4.70 to 4.85 (mt: 2H); 5.15 (dd, J=10 and 1.5 Hz: 1H); 5.19 (broad d, J=9 Hz: 1H); 5.23 (dd, J=17.5 and 1.5 Hz: 1H); 5.71 (ddd, J=16–8.5 and 5 Hz: 1H); 5.81 (dd, J=16.5 and 1.5 Hz: 1H); 5.88 (mt: 1H); 6.20 (d, J=16 Hz: 1H); 6.28 (mt: 1H); 6.49 (dd, J=16.5 and 5 Hz: 1H); 8.05 (s: 1H).

(16R)-14-O-Allyl-16-deoxo-16-hydroxy-pristinamycin II$_B$ was prepared in the following manner:

36.57 g of potassium carbonate and 65.35 cm$^3$ of allyl bromide were added to a solution of 20 g of (16R)-16-deoxo-16-hydroxypristinamycin II$_B$ in 450 cm$^3$ of 2-butanone, at 20° C. The reaction mixture was refluxed for 76 hours. After cooling to 20° C. and filtering, the reaction mixture was concentrated under reduced pressure (2.7 kPa). The residue was taken up in 200 cm$^3$ of dichloromethane and then washed successively twice with 100 cm$^3$ of water and 300 cm$^3$ of saturated aqueous sodium chloride solution. The organic phase was dried over magnesium sulfate and then concentrated to dryness under reduced pressure (2.7 kPa) to give 27.8 g of a yellow foam, which was purified by flash chromatography on silica [eluent: dichloromethane/acetonitrile/methanol (94/3/3 by volume)]. After concentrating the fractions containing the expected product, 7.80 g of (16R)-14-O-allyl-16-deoxo-16-hydroxypristinamycin II$_B$ were obtained in the form of a yellow foam.

$^1$H NMR spectrum (400 MHz, CDCl$_3$, δ in ppm): 0.96 (d, J=6.5 Hz: 3H); 1.00 (d, J=6.5 Hz: 3H); 1.10 (d, J=6.5 Hz: 3H); from 1.70 to 2.05 (mt: 6H); 1.80 (s: 3H); 2.12 (mt: 1H); 2.74 (mt: 1H); 2.79 (dd, J=16.5 and 5.5 Hz: 1H); 2.99 (dd, J=16.5 and 7 Hz: 1H); 3.15 (d, J=3 Hz: 1H); 3.42 (dd, J=16–10 and 4 Hz: 1H); from 3.80 to 3.95 (mt: 2H); from 3.95 to 4.10 (mt: 2H); 4.27 (mt: 1H); from 4.45 to 4.60 (mt: 2H); 4.78 (dd, J=10 and 1.5 Hz: 1H); 4.83 (dd, J=9 and 3.5 Hz: 1H); 5.18 (dd, J=10.5 and 1.5 Hz: 1H); 5.25 (dd, J=18 and 1.5 Hz: 1H); 5.34 (broad d, J=9 Hz: 1H); 5.65 (ddd, J=16–10 and 4.5 Hz: 1H); 5.79 (dd, J=16 and 1.5 Hz: 1H); from 5.85 to 6.00 (mt: 2H); 6.22 (broad d, J=16 Hz: 1H); 6.51 (dd, J=16 and 5 Hz: 1H); 8.15 (s: 1H).

(16R)-16-Deoxo-16-hydroxypristinamycin II$_B$ was prepared in the following manner:

A suspension of 11.35 g of sodium borohydride in 550 cm$^3$ of dichloromethane was refluxed for 20 minutes. 68.6 cm$^3$ of acetic acid were then added dropwise over about 30 minutes, followed by addition of a solution (predried over sodium sulfate) of 52.75 g of pristinamycin II$_B$ in 230 cm$^3$ of dichloromethane, over about 45 minutes. The reaction mixture was stirred for 4.5 hours at reflux and then for 16 hours at 20° C. 500 cm$^3$ of dichloromethane and 1500 cm$^3$ of water were then added to the reaction mixture. The organic phase was separated out after settling had taken place and the aqueous phase was extracted with 500 cm³ of methylene chloride. The organic phases were combined and the pH was adjusted to 8 by slow addition of 1000 cm³ of saturated aqueous sodium bicarbonate solution. The resulting organic phase was washed successively with 1000 cm³ of water and 1000 cm³ of saturated aqueous sodium chloride solution and then treated with 3S vegetable charcoal, dried over sodium sulfate, filtered through Celite® and concentrated to dryness under reduced pressure (2.7 kPa) to give 50 g of a pale yellow solid. 378 cm³ of aqueous 0.5 M ammonium hydroxide solution were added to a solution of the above solid in 900 cm³ of methylene chloride, at 20° C. After stirring for 16 hours at 20° C., the organic phase was separated out after settling had taken place, washed with 1000 cm³ of water and then with 1000 cm³ of saturated aqueous sodium chloride solution, dried over sodium sulfate, filtered and concentrated to dryness under reduced pressure (2.7 kPa) to give 46 g of a pale yellow solid, which was purified by flash chromatography on silica [eluent: methylene chloride/methanol gradient (98/2 and 97/3 by volume)]. After concentrating the fractions containing the expected product, 8.57 g of (16R)-16-deoxy-16-hydroxypristinamycin $II_B$ were obtained in the form of an off-white foam melting at about 140° C. (dec.).

$^1$H NMR spectrum (400 MHz, CDCl$_3$, δ in ppm): 0.96 (d, J=6.5 Hz: 3H); 1.00 (d, J=6.5 Hz: 3H); 1.10 (d, J=6.5 Hz: 3H); from 1.70 to 2.05 (mt: 6H); 1.81 (s: 3H); from 2.05 to 2.20 (mt: 2H); 2.76 (mt: 1H); 2.84 (dd, J=16 and 5.5 Hz: 1H); 3.00 (dd, J=16 and 7 Hz: 1H); 3.04 (d, J=4 Hz: 1H); 3.45 (ddd, J=16–9 and 4 Hz: 1H); 3.90 (mt: 1H); 4.04 (mt: 1H); 4.27 (mt: 1H); 4.48 (ddd, J=16–9 and 4 Hz: 1H); 4.80 (dd, J=10 and 2 Hz: 1 H); 4,84 (dd, J=9 and 3.5 Hz: 1H); 4.88 (mt: 1H); 5.44 (broad d, J=9 Hz: 1H); 5.67 (ddd, J=16–9 and 4 Hz: 1H); 5.80 (dd, J=16 and 1.5 Hz: 1H); 5.95 (dd, J=9 and 4 Hz: 1H); 6.19 (broad d, J=16 Hz: 1H); 6.53 (dd, J=16 and 5 Hz: 1H); 8.16 (s: 1H).

EXAMPLE 2

(16R)-16-Deoxo-16-methoxypristinamycin $II_B$ 1.2 g of sodium hydroxide, 0.50 g of tetra-n-butylammonium bromide and 4.70 cm³ of iodomethane were added to a solution of 8 g of (16R)-16-deoxo-16-hydroxypristinamycin $II_B$ (prepared as described in Example 1) in 40 cm³ of dichloromethane and 40 cm³ of water, at 25° C. The reaction mixture was stirred for 24 hours at room temperature and the phases were then separated after settling had taken place. The organic phase was washed 3 times with 100 cm³ of saturated aqueous sodium chloride solution and then dried over magnesium sulfate, filtered and concentrated under reduced pressure (2.7 kPa) to give 10.7 g of a cream-colored foam which was purified by flash chromatography on silica [eluent: dichloromethane/acetonitrile/methanol (95/2.5/2.5 by volume)]. After concentrating the fractions containing the expected product, 1.2 g of a pale yellow foam are obtained, which product was recrystallized from 7 cm³ of hot acetonitrile to give 1.15 g of (16R)-16-deoxo-16-methoxypristinamycin $II_B$ in the form of white crystals which melted at about 125° C. (dec.).

$^1$H NMR spectrum (400 MHz, CDCl$_3$, δ in ppm): 0.96 (d, J=6.5 Hz: 3H); 1.00 (d, J=6.5 Hz: 3H); 1.08 (d, J=6.5 Hz: 3H); 1.70 (ddd, J=14–7 and 3 Hz: 1H); from 1.75 to 2.05 (mt: 5H); 1.82 (s: 3H); 1.92 (d, J=4 Hz: 1H); 2.14 (mt: 1H); 2.75 (mt: 1H); 2.80 (dd, J=16 and 8.5 Hz: 1H); 3.18 (dd, J=16 and 4 Hz: 1H); 3.45 (s: 3H); 3.50 (mt: 1H); 3.75 (mt: 1H); 3.95 (mt: 2H); 4.45 (mt: 1H); 4.70 (mt: 1H); from 4.75 to 4.85 (mt: 2H); 5.36 (broad d, J=9 Hz: 1H); 5.72 (ddd, J=16–8 and 4.5 Hz: 1H); 5.81 (dd, J=16.5 and 1.5 Hz: 1H); 6.06 (mt: 1H); 6.18 (d, J=16 Hz: 1H); 6.51 (dd, J=16.5 and 5 Hz: 1H); 8.10 (s, 1H).

EXAMPLE 3

(16R)-16-Allyloxy-16-deoxopristinamycin $II_B$ 1.06 g of sodium hydroxide, 0.40 g of tetra-n-butylammonium bromide and 11.49 cm³ of allyl bromide were added to a solution of 7 g of (16R)-16-deoxo-16-hydroxypristinamycin $II_B$ (prepared as described in Example 1) in 50 cm³ of dichloromethane and 50 cm³ of water, at 25° C. The reaction mixture was stirred for 24 hours at room temperature and the phases were then separated once settling had taken place. The organic phase was washed twice with 100 cm³ of saturated aqueous sodium chloride solution and then dried over magnesium sulfate, filtered and concentrated under reduced pressure (2.7 kPa) to give 7.15 g of a yellow foam, which was purified by flash chromatography on silica [eluent: dichloromethane/acetonitrile/methanol (95/2.5/2.5 by volume)]. After concentrating the fractions containing the expected product, 1.2 g of a white foam were obtained, which product was recrystallized from 5 cm³ of hot acetonitrile to give 0.68 g of (16R)-16-allyloxy-16-deoxopristinamycin $II_B$ in the form of white crystals which melted at about 114° C. (dec.).

$^1$H NMR spectrum (400 MHz, CDCl$_3$, δ in ppm): 0.96 (d, J=6.5 Hz: 3H); 1.00 (d, J=6.5 Hz: 3H); 1.08 (d, J=6.5 Hz: 3H); 1.73 (ddd, J=15–7.5 and 3 Hz: 1H); from 1.75 to 2.05 (mt: 5H); 1.81 (s: 3H); 2.14 (mt: 1H); 2.74 (mt: 1H); 2.82 (dd, J=16 and 8.5 Hz: 1H); 3.16 (dd, J=16 and 3.5 Hz: 1H); 3.50 (ddd, J=16–8.5 and 3.5 Hz: 1H); 3.91 (mt: 1H); 3.94 (mt: 2H); 4.00 (resolved dd, J=12.5 and 5.5 Hz: 1H); 4.17 (resolved dd, J=12.5 and 5.5 Hz: 1H); 4.45 (ddd, J=16–9 and 5 Hz: 1H); 4.71 (mt: 1H); 4.76 (dd, J=9 and 3.5 Hz: 1H); 4.78 (dd, J=10 and 1.5 Hz: 1H); 5.22 (dd, J=10 and 1.5 Hz: 1H); 5.32 (dd, J=17.5 and 1.5 Hz: 1H); 5.35 (broad d, J=9 Hz: 1H (ddd, J=16–8.5 and 5 Hz: 1H); 5.81 (dd, J=16 and 1.5 Hz: 1H); 5.96 (mt: 1H); 6.11 (mt: 1H); 6.17 (broad d, J=16 Hz: 1H); 6.51 (dd, J=16 and 5 Hz: 1H); 8.08 (s: 1H).

EXAMPLE 4

(16R)-16-Deoxo-16-(prop-2-ynyloxy)pristinamycin $II_B$

Working in a similar manner to that described in Example 2, but starting with 7 g of (16R)-16-deoxo-16-hydroxypristinamycin $II_B$ dissolved in 40 cm³ of dichloromethane, 1.7 g of tetra-n-butylammonium bromide, 1.06 g of sodium hydroxide, 40 cm³ of water and 5 cm³ of propargyl bromide were added, at 20° C. and under an argon atmosphere. After stirring for 18 hours and work-up, 7.23 g of an orange solid were obtained, which product was purified by flash chromatography on silica [eluent: dichloromethane/methanol/acetonitrile (95/2.5/2.5 by volume)]. After concentrating the fractions containing the expected product, 1.58 g of a yellow solid were obtained, which product was recrystallized from 40 cm³ of hot acetonitrile. After filtering off the crystals through a No. 4 sinter funnel with 40 cm³ of acetonitrile and drying under reduced pressure (2.7 kPa), 1.36 g of (16R)-16-deoxo-16-(prop-2-ynyloxy)pristinamycin $II_B$ were obtained in the form of white crystals which melted at about 112° C. with decomposition.

¹H NMR spectrum (400 MHz, CDCl₃, δ in ppm): 0.96 (d, J=6.5 HZ: 3H); 1.01 (d, J=6.5 Hz: 3H); 1.08 (d, J=6.5 Hz: 3H); 1.75 (ddd, J=16–7.5 and 3.5 Hz: 1H); from 1.75 to 2.05 (mt: 5H); 1.84 (s: 3H); 1.85 (d, J=3.5 Hz: 1H); 2.15 (mt: 1H); 2.48 (t, J=2.5 Hz: 1H); 2.75 (mt: 1H); 2.87 (dd, J=16 and 9 Hz: 1H); 3.21 (dd, J=16 and 3.5 Hz: 1H); 3.50 (ddd, J=16–8 and 3.5 Hz: 1H); 3.94 (mt: 2H); 4.09 (mt: 1H); 4.25 (dd, J=16 and 2.5 Hz: 1H); 4.31 (dd, J=16 and 2.5 Hz: 1H); 4.46 (mt: 1H); from 4.65 to 4.80 (mt: 2H); 4.78 (dd, J=10 and 1.5 Hz: 1H); 5.36 (broad d, J=9 Hz: 1H); 5.74 (ddd, J=16–8.5 and 5 Hz: 1H); 5.82 (dd, J=16 and 1.5 Hz: 1H); from 6.10 to 6.25 (mt: 1H); 6.18 (broad d, J=16 Hz: 1H); 6.51 (dd, J=16 and 5.5 Hz: 1H); 8.10 (s, 1H).

EXAMPLE 5

(16R)-16-Deoxo-16-methoxypristinamycin $II_A$

Working in a manner similar to that described in Example 2, but starting with a solution of 8 g of (16R)-16-deoxo-16-hydroxypristinamycin $II_A$ in 40 cm³ of dichloromethane and 40 cm³ of water, 1.2 g of sodium hydroxide, 0.49 g of tetra-n-butylammonium bromide and 4.7 cm³ of methyl iodide were added, at 25° C. After stirring for 96 hours and work-up, and after purification by flash chromatography on silica [eluent: dichloromethane/acetonitrile/methanol (96/2/2 by volume)] and concentrating the fractions containing the expected product, 0.38 g of a foam was obtained, which was diluted in 40 cm³ of ethyl acetate and then washed successively with 20 cm³ of 0.1 N hydrochloric acid solution, 20 cm³ of water and 20 cm³ of saturated aqueous sodium chloride solution. The organic phase was dried over magnesium sulfate, filtered and concentrated under reduced pressure (2.7 kPa) to give 0.15 g of (16R)-16-deoxo-16-methoxypristinamycin $II_A$ in the form of a white powder which melted at about 151° C. with decomposition.

¹H NMR spectrum (300 MHz, CDCl₃, δ in ppm): 0.98 (d, J=6.5 Hz: 3H); 1.00 (d, J=6.5 Hz: 3H); 1.13 (d, J=6.5 Hz: 3H); 1.50 (d, J=3.5 Hz: 1H); 1.75 (d, J=1Hz: 3H); 1.88 (ddd, J=16–10.5 and 3 Hz: 1H); from 1.95 to 2.10 (mt: 2H); from 2.60 to 2.90 (mt: 4 H); 3.14 (dd, J=14 and 3 Hz: 1H); 3.26 (mt: 1H); 3.44 (s: 3H); 3.87 (very broad d, J=17 Hz: 1H); from 4.15 to 4.45 (mt: 3H); 4.53 (mt: 1H); 4.86 (broad d, J=9 Hz: 1H); 4.96 (dd, J=10 and 2 Hz: 1H); 5.66 (ddd, J=16–5 and 3.5 Hz: 1H); 5.93 (broad d, J=16 Hz: 1H); 6.02 (dd, J=16.5 and 1 Hz: 1H); 6.14 (t, J=3 Hz: 1H); 6.62 (dd, J=16.5 and 7.5 Hz: 1H); from 7.25 to 7.40 (mf: 1H); 7.89 (s, 1H).

(16R)-16-Hydroxypristinamycin $II_A$ may be prepared, for example, according to F. Le Goffic et. al., Transformations of Pristinamycin II to Study Its Mechanism of Action, 16(1) Eur. J. Medicinal Chemistry 69 (January–February 1981).

The present invention also relates to pharmaceutical compositions comprising at least one streptogramin group A derivative according to the invention, in pure form, combined with at least one group B streptogramin derivative, where appropriate in the form of a salt, and/or in the form of a combination with at least one compatible and pharmaceutically acceptable diluent or adjuvant.

The compositions according to the invention may be used, for example, orally, parenterally, topically, rectally or as aerosols.

Solid compositions for oral administration which may be used include, for example, tablets, pills, gel capsules, powders and granules. In these compositions, the active product according to the invention, generally in the form of a combination, can be mixed with at least one inert diluent or adjuvant, such as, for example, sucrose, lactose or starch. These compositions may comprise substances other than diluents, for example, a lubricant such as magnesium stearate or a coating intended for controlled release.

Liquid compositions for oral administration which may be used include, for example, pharmaceutically acceptable solutions, suspensions, emulsions, syrups and elixirs containing inert diluents such as water or liquid paraffin. These compositions may also comprise substances other than diluents, such as, for example, wetting, sweetening or flavoring products.

The compositions for parenteral administration may be, for example, sterile solutions or emulsions. Solvents or vehicles which may be used include, for example, propylene glycol, polyethylene glycol, plant oils, such as, for example, olive oil, and injectable organic esters, for example, ethyl oleate. These compositions may also comprise at least one adjuvant, such as, for example, adjuvants chosen from wetting agents, isotonic agents, emulsifiers, dispersants, and stabilizers.

The sterilization may be carried out in several ways, for example, using a bacteriological filter, by irradiation, or by heating. The compositions may also be prepared in the form of sterile solid compositions which may be dissolved at the time of use in sterile water or any other injectable sterile medium.

The compositions for topical administration may be, for example, in the form of creams, ointments, lotions or aerosols.

The compositions for rectal administration may be, for example, suppositories or rectal capsules which contain, besides the active principle, excipients such as cocoa butter, semisynthetic glycerides or polyethylene glycols.

The compositions may also be aerosols. For use in the form of liquid aerosols, the compositions may be stable sterile solutions or solid compositions dissolved at the time of use in apyrogenic sterile water, in saline or any other pharmaceutically acceptable vehicle. For use in the form of dry aerosols for direct inhalation, the active principle was finely divided and combined with a solid water-soluble diluent or vehicle with a particle size ranging, for example, from 30 to 80 μm, for example, dextran, mannitol or lactose.

In human therapy, for example, the novel streptogramin derivatives according to the invention can be used for treating infections of bacterial origin. The doses depend on the desired effect and the duration of the treatment. The doctor will determine the dosage(s) that he considers to be most suitable depending on the treatment, as a function of the age, weight, degree of infection and the other factors specific to the individual to be treated. Generally, for example, the doses can range from 0.5 to 3 g of active product in 2 or 3 administrations per day, via the oral or parenteral route for an adult.

The example which follows illustrates a composition according to the invention, without however exhibiting a limiting character.

EXAMPLE

Tablets containing a 250 mg dose of active product and having the composition below can be prepared according to known, art-recognized techniques:

| | |
|---|---|
| (16R)-16-Deoxo-16-methoxy-pristinamycin $II_B$ | 175 mg |
| Pristinamycin $I_B$ | 75 mg |

-continued

| Excipient: starch, hydrated silica, dextrin, gelatin, magnesium stearate: qs | 500 mg |

What is claimed is:

1. A pharmaceutical composition comprising at least one group A streptogramin compound of formula (I) or a salt thereof:

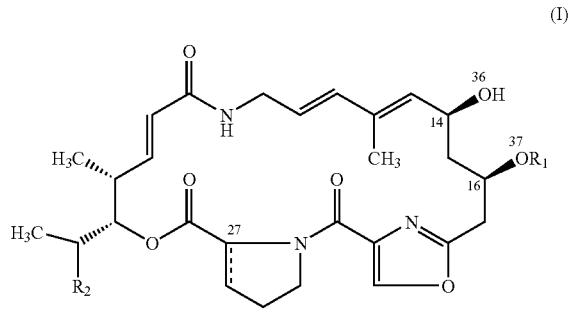

wherein:
R₁ is chosen from alkyl groups, alkenyl groups, alkynyl groups, monofluoro substituted alkyl groups, monofluoro substituted alkenyl groups, monofluoro substituted alkynyl groups, polyfluoro substituted alkyl groups, polyfluoro substituted alkenyl groups, polyfluoro substituted alkynyl groups, $C_3$–$C_6$ cycloalkyl groups, a phenylmethyl group, and heterocyclylmethyl groups, wherein said heterocyclyl portion is aromatic,
R₂ is chosen from a hydrogen atom, a methyl group, and an ethyl group,
the bond

- - - - - is a single bond (27R stereochemistry) or a double bond,
unless otherwise stated, said alkyl groups are chosen from straight and branched $C_1$–$C_6$ alkyl groups,
unless otherwise stated, said alkenyl groups are chosen from straight and branched $C_3$–$C_6$ alkenyl groups, and
unless otherwise stated, said alkynyl groups are chosen from straight and branched $C_3$–$C_6$ alkynyl groups,
and at least one natural, semi-synthetic or synthetic group B streptogramin compound or salt thereof.

2. The pharmaceutical composition according to claim 1, wherein said natural group B streptogramin compound is obtained from a genetically modified strain.

3. The pharmaceutical composition according to claim 1, wherein said at least one natural group B streptogramin compound or salt thereof is chosen from pristinamycin IA, pristinamycin IB, pristinamycin IC, pristinamycin ID, pristinamycin IE, pristinamycin IF, pristinamycin IG, virginiamycin S1, virginiamycin S3, virginiamycin S4, vernamycin B, vernamycin C, and etamycin.

4. The pharmaceutical composition according to claim 1, wherein said at least one natural group B streptogramin compound or salt thereof is pristinamycin IA.

5. The pharmaceutical composition according to claim 1, wherein said at least one natural group B streptogramin compound or salt thereof is chosen from pristinamycin IB.

6. The pharmaceutical composition according to claim 1, wherein said at least one natural group B streptogramin compound or salt thereof is chosen from pristinamycin IC.

7. The pharmaceutical composition according to claim 1, wherein said at least one natural group B streptogramin compound or salt thereof is chosen from pristinamycin ID.

8. The pharmaceutical composition according to claim 1, wherein said at least one natural group B streptogramin compound or salt thereof is chosen from pristinamycin IE.

9. The pharmaceutical composition according to claim 1, wherein said at least one natural group B streptogramin compound or salt thereof is chosen from pristinamycin IF.

10. The pharmaceutical composition according to claim 1, wherein said at least one natural group B streptogramin compound or salt thereof is chosen from pristinamycin IG.

11. The pharmaceutical composition according to claim 1, wherein said at least one natural group B streptogramin compound or salt thereof is chosen from virginiamycin S1.

12. The pharmaceutical composition according to claim 1, wherein said at least one natural group B streptogramin compound or salt thereof is chosen from, virginiamycin S3.

13. The pharmaceutical composition according to claim 1, wherein said at least one natural group B streptogramin compound or salt thereof is chosen from virginiamycin S4.

14. The pharmaceutical composition according to claim 1, wherein said at least one natural group B streptogramin compound or salt thereof is chosen from vernamycin B.

15. The pharmaceutical composition according to claim 1, wherein said at least one natural group B streptogramin compound or salt thereof is chosen from vernamycin C.

16. The pharmaceutical composition according to claim 1, wherein said at least one natural group B streptogramin compound or salt thereof is chosen from etamycin.

17. The pharmaceutical composition according to claim 1, further comprising at least one agent chosen from pharmaceutically acceptable diluents and pharmaceutically acceptable adjuvants.

18. A pharmaceutical composition comprising at least one group A streptogramin compound of formula (I) or a salt thereof:

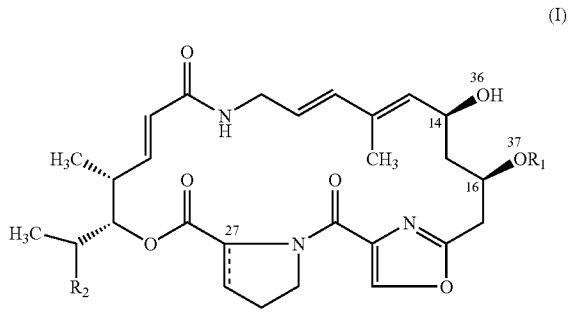

wherein:
R₁ is chosen from alkyl groups, alkenyl groups, alkynyl groups, monofluoro substituted alkyl groups, monofluoro substituted alkenyl groups, monofluoro substituted alkynyl groups, polyfluoro substituted alkyl groups, polyfluoro substituted alkenyl groups, polyfluoro substituted alkynyl groups, $C_3$–$C_6$ cycloalkyl groups, a phenylmethyl group, and heterocyclylmethyl groups, wherein said heterocyclyl portion is aromatic, $R_2$ is chosen from a hydrogen atom, a methyl group, and an ethyl group, the bond

----- is a single bond (27R stereochemistry) or a double bond, unless otherwise stated, said alkyl groups are chosen from straight and branched $C_1$–$C_6$ alkyl groups, unless otherwise stated, said alkenyl groups are chosen from straight and branched $C_3$–$C_6$ alkenyl groups, and unless otherwise stated, said alkynyl groups are chosen from straight and branched $C_3$–$C_6$ alkynyl groups, and one natural group B streptogramin compound or salt thereof, which is pristinamycin IA, and wherein pristinamycin IA is obtained from a genetically modified strain.

19. The pharmaceutical composition according to claim 18, further comprising at least one agent chosen from pharmaceutically acceptable diluents and pharmaceutically acceptable adjuvants.

* * * * *